United States Patent
Desenne et al.

(10) Patent No.: US 9,707,415 B2
(45) Date of Patent: Jul. 18, 2017

(54) USE OF VOLATILE LINEAR ALKANE(S) AND LIQUID FATTY ESTER(S) IN AN ANHYDROUS MEDIUM FOR THE TREATMENT OF KERATIN FIBRES, AND AN ANHYDROUS COMPOSITION BASED ON VOLATILE LINEAR ALKANE(S), LIQUID FATTY ESTER(S) AND PARTICULAR OIL(S)

(75) Inventors: Patricia Desenne, Pringy (FR); Claire Bourdin, Levallois Perret (FR); Charles Gringore, Asnieres-sur-Seine (FR)

(73) Assignee: L'OREAL, Paris (FR)

( * ) Notice: Subject to any disclaimer, the term of this patent is extended or adjusted under 35 U.S.C. 154(b) by 118 days.

(21) Appl. No.: 12/975,632

(22) Filed: Dec. 22, 2010

(65) Prior Publication Data

US 2012/0003172 A1  Jan. 5, 2012

Related U.S. Application Data

(60) Provisional application No. 61/296,486, filed on Jan. 20, 2010.

(30) Foreign Application Priority Data

Dec. 23, 2009 (FR) ...................... 09 59483

(51) Int. Cl.
*A61K 8/00* (2006.01)
*A61Q 5/12* (2006.01)
*A61K 8/31* (2006.01)
*A61K 8/37* (2006.01)
*A61K 8/891* (2006.01)

(52) U.S. Cl.
CPC .................. *A61Q 5/12* (2013.01); *A61K 8/31* (2013.01); *A61K 8/37* (2013.01); *A61K 8/891* (2013.01); *A61K 2800/31* (2013.01)

(58) Field of Classification Search
CPC ... A61Q 5/12; A61K 8/31; A61K 8/37; A61K 8/891; A61K 2800/31
See application file for complete search history.

(56) References Cited

U.S. PATENT DOCUMENTS

2010/0015073 A1* 1/2010 Clavel et al. .................. 424/63
2010/0183536 A1* 7/2010 Ansmann et al. ............. 424/65

FOREIGN PATENT DOCUMENTS

DE  10 2008 012 457  12/2008
WO  WO 2010/026140  3/2010

OTHER PUBLICATIONS

French Search Report issued Aug. 11, 2010, in FR 09 59483, filed Dec. 23, 2009.
U.S. Appl. No. 12/977,183, filed Dec. 23, 2010, Desenne, et al.
U.S. Appl. No. 12/969,980, filed Dec. 16, 2010, Desenne, et al.
U.S. Appl. No. 12/975,705, filed Dec. 22, 2010, Desenne, et al.
U.S. Appl. No. 12/970,988, filed Dec. 17, 2010, Desenne, et al.
U.S. Appl. No. 12/977,257, filed Dec. 23, 2010, Desenne, et al.
U.S. Appl. No. 12/977,204, filed Dec. 23, 2010, Desenne, et al.
U.S. Appl. No. 12/977,227, filed Dec. 23, 2010, Desenne, et al.
U.S. Appl. No. 14/683,345, filed Apr. 10, 2015, Desenne, et al.

* cited by examiner

*Primary Examiner* — Nannette Holloman
(74) *Attorney, Agent, or Firm* — Oblon, McClelland, Maier & Neustadt, L.L.P.

(57) ABSTRACT

Use, for the cosmetic treatment of keratin fibers such as the hair, of at least one volatile linear alkane and at least one liquid fatty ester of $C_{1-30}$ mono- or dicarboxylic acid and of a $C_{1-30}$ monohydric alcohol in an anhydrous medium, in a weight ratio of volatile linear alkane(s) to liquid fatty ester(s) of less than 5. Anhydrous composition comprising:
 at least one volatile linear alkane,
 at least one liquid fatty ester of a $C_{1-30}$ mono- or dicarboxylic acid and of a $C_{1-30}$ monohydric alcohol in a weight ratio of volatile linear alkane(s) to liquid fatty ester(s) of less than 5, and
 at least one oil selected from vegetable oils and silicone oils.

15 Claims, No Drawings

USE OF VOLATILE LINEAR ALKANE(S) AND LIQUID FATTY ESTER(S) IN AN ANHYDROUS MEDIUM FOR THE TREATMENT OF KERATIN FIBRES, AND AN ANHYDROUS COMPOSITION BASED ON VOLATILE LINEAR ALKANE(S), LIQUID FATTY ESTER(S) AND PARTICULAR OIL(S)

REFERENCE TO PRIOR APPLICATIONS

This application claims priority to U.S. provisional application Ser. No. 61/296,486, filed Jan. 20, 2010; and to French patent application 09 59483, filed Dec. 23, 2009, both incorporated herein by reference.

FIELD OF THE INVENTION

The present invention relates to the use, for example for the cosmetic treatment of keratin fibres, such as the hair, of one or more volatile linear alkane(s) and of one or more liquid fatty ester(s) in a weight ratio of volatile linear alkane(s) to liquid fatty ester(s) of less than 5, in an anhydrous medium, to an anhydrous cosmetic composition based on volatile linear alkane(s), liquid fatty ester(s) and particular oil(s), the weight ratio of volatile linear alkane(s) to liquid fatty ester(s) being less than 5, and to a method of cosmetic treatment employing said composition.

BACKGROUND OF THE INVENTION

In the field of hair treatment, the use of volatile solvents is known in hair products for care and for shine. They are generally used for various reasons. They notably make it possible to modify the sensory perception of a hair product by endowing it with a texture that is light and non-sticky to the touch. They can also impart a slippery nature, which facilitates distribution of the product on the hair and in particular on dry hair.

These volatile solvents, which are generally liquid fatty esters, hydrocarbon oils of the isododecane or isohexadecane type, and/or silicone oils, can notably lead to problems of a greasy feel, lack of shine, and hair that is stiff and hard.

Moreover, these volatile solvents are generally present at a high concentration in anhydrous products. They can then have the drawback of a negative impact on the environment, notably on the aquatic environment.

There is therefore still a need to replace these volatile solvents, to avoid the drawbacks mentioned above.

DETAILED DESCRIPTION OF THE PREFERRED EMBODIMENTS

It has now been discovered, unexpectedly and surprisingly, that by using one or more volatile linear alkane(s) and one or more liquid fatty ester(s) of $C_{1-30}$ mono- or dicarboxylic acid and of $C_{1-30}$ monohydric alcohol in an anhydrous medium, in a weight ratio of volatile linear alkane(s) to liquid fatty ester(s) of less than 5, it was possible to avoid transfer of the product onto the hands after passing the hands through the hair and the drawbacks mentioned above, and to improve the cosmetic properties of the hair such as smoothness, shine, ease of shaping, disentangling, lightness, suppleness and feel.

In particular, application on wet hair gives hair that is smoother and shinier. Moreover, when the composition is used on dry hair, the hair becomes shinier, and can be shaped more easily.

Thus, the invention relates to the use, for the cosmetic treatment of keratin fibres, such as the hair, of one or more volatile linear alkanes and one or more liquid fatty esters of $C_{1-30}$ mono- or dicarboxylic acid and of $C_{1-30}$ monohydric alcohol, in an anhydrous medium, in a weight ratio of volatile linear alkane(s) to liquid fatty ester(s) of less than 5.

It also relates to a cosmetic composition comprising, in an anhydrous medium:
 one or more volatile linear alkanes,
 one or more liquid fatty esters of a $C_{12-30}$ mono- or dicarboxylic acid and of a $C_{1-30}$ monohydric alcohol, in a weight ratio of volatile linear alkane(s) to liquid fatty ester(s) of greater than or equal to 0.1 and less than 5, and
 one or more oils selected from silicone oils.

Another object of the invention is a method of cosmetic treatment of keratinous materials, such as keratin fibres, for example the hair, employing said composition.

According to the invention, one or more volatile linear alkanes are used in combination with one or more liquid fatty esters of $C_{1-30}$ mono- or dicarboxylic acid and $C_{1-30}$ monohydric alcohol, in an anhydrous medium, in a weight ratio of volatile linear alkane(s) to liquid fatty ester(s) of less than 5, for the cosmetic treatment of keratin fibres, such as the hair. This use notably gives better properties of smoothness, shine, ease of shaping, disentangling, lightness, suppleness and/or feel.

"One or more volatile linear alkane(s)" means indiscriminately "one or more volatile linear alkane oils".

A volatile linear alkane suitable for the invention is liquid at room temperature (about 25° C.) and at atmospheric pressure (101 325 Pa or 760 mmHg).

"Volatile linear alkane" suitable for the invention means a linear alkane that can evaporate in contact with the skin in less than one hour, at room temperature (25° C.) and atmospheric pressure (101 325 Pa), which is liquid at room temperature, and notably has a rate of evaporation in the range from 0.01 to 15 mg/cm²/min, at room temperature (25° C.) and atmospheric pressure (101 325 Pa).

Preferably, the volatile linear alkanes suitable for the invention have a rate of evaporation in the range from 0.01 to 3.5 mg/cm²/min, more preferably from 0.01 to 1.5 mg/cm²/min, at room temperature (25° C.) and atmospheric pressure (101 325 Pa).

More preferably, the volatile linear alkanes suitable for the invention have a rate of evaporation in the range from 0.01 to 0.8 mg/cm²/min, preferably from 0.01 to 0.3 mg/cm²/min, and even more preferably from 0.01 to 0.12 mg/cm²/min, at room temperature (25° C.) and atmospheric pressure (101 325 Pa).

The rate of evaporation of a volatile alkane according to the invention (and more generally of a volatile solvent) can notably be evaluated by means of the protocol described in WO 06/013413, and more particularly by means of the protocol described below.

15 g of volatile hydrocarbon solvent is introduced into a crystallizing dish (diameter: 7 cm) placed on a balance that is inside a chamber of about 0.3 m³ with controlled temperature (25° C.) and humidity (relative humidity 50%).

The volatile hydrocarbon solvent is allowed to evaporate freely, without stirring, providing ventilation by a fan (PAPST-MOTOREN, reference 8550 N, at a speed of 2700 rev/min) arranged in a vertical position above the crystallizing dish containing the volatile hydrocarbon solvent, with the blades directed towards the crystallizing dish, at a distance of 20 cm relative to the bottom of the crystallizing dish.

The mass of the volatile hydrocarbon solvent remaining in the crystallizing dish is measured at regular time intervals.

An evaporation profile of the solvent is then obtained by plotting the curve of the amount of product evaporated (in mg/cm$^2$) as a function of time (in min).

Then the rate of evaporation is calculated, corresponding to the tangent at the origin of the curve obtained. The rates of evaporation are expressed in mg of volatile solvent evaporated per unit area (cm$^2$) in unit time (minute).

According to a preferred embodiment, the volatile linear alkanes suitable for the invention have a non-zero vapour pressure (also called saturated vapour pressure), at room temperature, in particular a vapour pressure in the range from 0.3 Pa to 6000 Pa.

Preferably, the volatile linear alkanes suitable for the invention have a vapour pressure in the range from 0.3 to 2000 Pa, more preferably from 0.3 to 1000 Pa, at room temperature (25° C.).

More preferably, the volatile linear alkanes suitable for the invention have a vapour pressure in the range from 0.4 to 600 Pa, preferably from 1 to 200 Pa, and even more preferably from 3 to 60 Pa, at room temperature (25° C.).

According to one embodiment, a volatile linear alkane suitable for the invention can have a flash point in the range from 30 to 120° C., and more particularly from 40 to 100° C. The flash point is in particular measured according to standard ISO 3679.

According to one embodiment, the volatile linear alkanes suitable for the invention can be linear alkanes having from 7 to 15 carbon atoms, preferably from 8 to 14 carbon atoms and more preferably from 9 to 14 carbon atoms.

More preferably, the volatile linear alkanes suitable for the invention can be linear alkanes having from 10 to 14 carbon atoms, and even more preferably from 11 to 14 carbon atoms.

A volatile linear alkane suitable for the invention can advantageously be of vegetable origin.

Preferably, the volatile linear alkane or mixture of volatile linear alkanes present in the composition according to the invention comprises at least one isotope $^{14}$C of carbon (carbon 14). In particular, the $^{14}$C isotope can be present in a ratio by number of $^{14}$C/$^{12}$C isotopes (or $^{14}$C/$^{12}$C ratio) greater than or equal to $1 \cdot 10^{-16}$, preferably greater than or equal to $1 \cdot 10^{-15}$, more preferably greater than or equal to $7.5 \times 10^{-14}$, and even more preferably greater than or equal to $1.5 \times 10^{-13}$. Preferably, the $^{14}$C/$^{12}$C ratio is in the range from $6 \times 10^{-13}$ to $1.2 \times 10^{-12}$.

The quantity of $^{14}$C isotopes in the volatile linear alkane or mixture of volatile linear alkanes can be determined by methods known by a person skilled in the art such as Libby's counting method, liquid scintillation spectrometry or accelerator mass spectrometry.

Such an alkane can be obtained, directly or in several stages, from a vegetable raw material such as an oil, a butter, a wax, etc.

As examples of alkanes suitable for the invention, we may mention the alkanes described in patent applications WO 2007/068371 and WO2008/155059. These alkanes are obtained from fatty alcohols, themselves obtained from copra oil or palm oil.

As examples of volatile linear alkanes suitable for the invention, we may mention n-heptane (C7), n-octane (C8), n-nonane (C9), n-decane (C10), n-undecane (C11), n-dodecane (C12), n-tridecane (C13), n-tetradecane (C14), n-pentadecane (C15), and mixtures thereof. According to a particular embodiment, the volatile linear alkane is selected from n-nonane, n-undecane, n-dodecane, n-tridecane, n-tetradecane, and mixtures thereof.

According to a preferred embodiment, we may mention mixtures of n-undecane (C11) and of n-tridecane (C13) obtained in examples 1 and 2 of application WO2008/155059.

We may also mention the n-dodecane (C12) and n-tetradecane (C14) sold respectively under references PARAFOL 12-97 and PARAFOL 14-97 by the company Sasol, and mixtures thereof.

One embodiment consists of using a single volatile linear alkane.

Alternatively, it is possible to use a mixture of at least two different volatile linear alkanes, differing from one another by a number of carbons n of at least 1, in particular differing from one another by a number of carbons of 1 or 2.

According to one embodiment, a mixture of at least two different volatile linear alkanes is used, having from 10 to 14 carbon atoms and differing from one another by a number of carbons of at least 1. As examples, we may notably mention the mixtures of volatile linear alkanes C10/C11, C11/C12, or C12/C13.

According to another embodiment, a mixture of at least two different volatile linear alkanes is used, having from 10 to 14 carbon atoms and differing from one another by a number of carbons of at least 2. As examples, we may notably mention the mixtures of volatile linear alkanes C10/C12, or C12/C14, for an even number of carbons n and the mixture C11/C13 for an odd number of carbons n.

According to a preferred embodiment, a mixture of at least two different volatile linear alkanes is used, having from 10 to 14 carbon atoms and differing from one another by a number of carbons of at least 2, and in particular a mixture of volatile linear alkanes C11/C13 or a mixture of volatile linear alkanes C12/C14.

Other mixtures combining more than 2 volatile linear alkanes according to the invention, such as, for example, a mixture of at least 3 different volatile linear alkanes having from 7 to 15 carbon atoms and differing from one another by a number of carbons of at least 1, can be used in the invention.

In the case of mixtures of two volatile linear alkanes, said two volatile linear alkanes preferably represent more than 95% and more preferably more than 99 wt. % of the mixture.

According to a particular embodiment of the invention, in a mixture of volatile linear alkanes, the volatile linear alkane having the smallest number of carbons predominates in the mixture.

According to another embodiment of the invention, a mixture of volatile linear alkanes is used in which the volatile linear alkane having the largest number of carbons predominates in the mixture.

As examples of mixtures suitable for the invention, we may notably mention the following mixtures:
  from 50 to 90 wt. %, preferably from 55 to 80 wt. %, more preferably from 60 to 75 wt. % of volatile $C_n$ linear alkane, with n in the range from 7 to 15
  from 10 to 50 wt. %, preferably from 20 to 45 wt. %, preferably from 24 to 40 wt. % of volatile $C_{n+x}$ linear alkane, with x greater than or equal to 1, preferably x=1 or x=2, with n+x between 8 and 14,
relative to the total weight of the alkanes in said mixture.

In particular, said mixture of volatile linear alkanes can further contain:
  less than 2 wt. %, preferably less than 1 wt. % of branched hydrocarbons, and/or less than 2 wt. %, preferably less than 1 wt. % of aromatic hydrocarbons, and/or less than 2 wt. %, preferably less than 1 wt. % and preferably less than 0.1 wt. % of unsaturated hydrocarbons, said percentages being expressed relative to the total weight of the mixture.

More particularly, the volatile linear alkanes suitable for the invention can be used in the form of an n-undecane/n-tridecane mixture.

In particular, a mixture of volatile linear alkanes will be used comprising:

from 55 to 80 wt. %, preferably from 60 to 75 wt. % of volatile C11 (n-undecane) linear alkane and from 20 to 45 wt. %, preferably from 24 to 40 wt. % of volatile C13 (n-tridecane) linear alkane, relative to the total weight of the alkanes in said mixture.

According to a particular embodiment, the mixture of alkanes is an n-undecane/n-tridecane mixture. In particular, such a mixture can be obtained according to example 1 or example 2 of application WO 2008/155059.

According to another particular embodiment, the n-dodecane sold under reference PARAFOL 12-97 by SASOL is used.

According to another particular embodiment, the n-tetradecane sold under reference PARAFOL 14-97 by SASOL is used.

According to yet another embodiment, a mixture of n-dodecane and n-tetradecane is used.

"Liquid fatty ester" means, in the sense of the present invention, an ester of fatty acid and/or of fatty alcohol that is liquid at room temperature (25° C.) and atmospheric pressure (101 325 Pa).

The liquid fatty ester(s) used in the invention are fatty esters of a $C_{1-30}$, preferably $C_{12-30}$ and more preferably $C_{12-22}$, mono- or dicarboxylic acid and of a $C_{1-30}$, preferably $C_{1-20}$, monohydric alcohol.

In one embodiment of the invention, the liquid fatty ester has from 10 to 50 carbon atoms in total.

As examples of liquid fatty esters that can be used in the present invention, we may notably mention ethyl laurate, butyl laurate, hexyl laurate, isohexyl laurate, isopropyl laurate, methyl myristate, ethyl myristate, butyl myristate, isobutyl myristate, isopropyl myristate, 2-octyldodecyl myristate, 2-ethylhexyl monococoate (or octyl monococoate), ethyl palmitate, isopropyl palmitate, isobutyl palmitate, 2-ethylhexyl palmitate (or octyl palmitate), butyl stearate, isopropyl stearate, isobutyl stearate, isocetyl stearate, isostearyl isostearate, isopropyl isostearate, 2-ethylhexyl stearate (or octyl stearate), 2-ethylhexyl hydroxystearate (or octyl hydroxystearate), decyl oleate, diisopropyl sebacate, isononyl isononanoate, tridecyl neopentanoate, isocetyl neopentanoate, isostearyl neopentanoate, octyldodecyl neopentanoate and isoarachidyl neopentanoate and mixtures thereof.

Preferably, the liquid fatty ester used in the invention is selected from isopropyl myristate, methyl myristate, ethyl myristate, butyl myristate, isobutyl myristate, 2-octyldodecyl myristate, 2-ethylhexyl monococoate (or octyl monococoate), ethyl palmitate, isopropyl palmitate, isobutyl palmitate, 2-ethylhexyl palmitate (or octyl palmitate), butyl stearate, isopropyl stearate, isobutyl stearate, isocetyl stearate, isostearyl isostearate, isopropyl isostearate, 2-ethylhexyl stearate (or octyl stearate), 2-ethylhexyl hydroxystearate (or octyl hydroxystearate), decyl oleate and more particularly isopropyl myristate, isopropyl palmitate, and mixtures thereof.

The weight ratio of volatile linear alkane(s) to liquid fatty ester(s) is less than 5, and preferably greater than or equal to 0.1. In particular, the latter is in the range from 0.1 to 4.9, more preferably from 0.1 to 4.7.

"Anhydrous medium" means, in the sense of the present invention, a medium having a water content below 5 wt. %, preferably below 2 wt. %, even more particularly below 1 wt. %, relative to the total weight of the composition. It should be noted that the water may also be in the form of bound water, as water of crystallization of salts or as traces of water adsorbed by the raw materials used within the scope of the invention. This medium can comprise one or more organic solvents.

As organic solvents that may be present in the anhydrous medium, we may mention for example linear or branched $C_2$-$C_4$ alcohols, such as ethanol and isopropanol; glycerol; polyols and ethers of polyols such as 2-butoxyethanol, propylene glycol, dipropylene glycol, monomethyl ether of propylene glycol, monoethyl ether and monomethyl ether of diethylene glycol; as well as aromatic alcohols such as benzyl alcohol or phenoxyethanol; and mixtures thereof.

The invention also relates to a cosmetic composition comprising, in an anhydrous medium:

one or more volatile linear alkanes, one or more liquid fatty esters of a $C_{12-30}$ mono- or dicarboxylic acid and of a $C_{1-30}$ monohydric alcohol in a weight ratio of volatile linear alkane(s) to liquid fatty ester(s) of greater than or equal to 0.1 and less than 5, and one or more oils selected from silicone oils.

The anhydrous medium, the volatile linear alkanes, the liquid fatty esters and the weight ratio of volatile linear alkane(s) to liquid fatty ester(s) are as defined above.

The composition of the invention can comprise from 0.5 to 90 wt. % of volatile linear alkane(s), in particular from 1 to 70 wt. %, and more particularly from 2 to 70 wt. %, and preferably from 15 to 70 wt. % of volatile linear alkane(s) relative to the total weight of the composition.

The liquid fatty ester or esters of a $C_{1-30}$, preferably $C_{12-30}$, more preferably $C_{12-22}$, mono- or dicarboxylic acid and of a $C_{1-30}$, preferably $C_{1-20}$ monohydric alcohol is/are present preferably in an amount from 0.1 to 90 wt. %, more particularly from 1 to 80%, and more preferably from 10 to 80 wt. % relative to the total weight of the composition.

"Oil" means any lipophilic, non-ionic compound, insoluble in water and liquid at room temperature (25° C.) and atmospheric pressure (760 mmHg, or 101 325 Pa). "Insoluble in water" means, in the sense of the present invention, a compound whose solubility at spontaneous pH in water at 25° C. and atmospheric pressure is less than 1% and preferably less than 0.5 wt. %. The oils are soluble in organic solvents in the same conditions of temperature and pressure, for example chloroform, ethanol or benzene. Moreover, the oils are liquid at normal temperature (25° C.) and at atmospheric pressure. The oils preferably have a melting point below 5° C.

The oils used in the present invention preferably have a dynamic viscosity at 25° C. of less than 1 Pa·s (1000 cP), preferably between $10^{-3}$ and 0.1 Pa·s (1 and 100 cP). The dynamic viscosity is measured at 25° C. at a shear rate of 100 $s^1$, for example with the apparatus with the reference RM 180 Rheomat from the company METTLER.

The oils that can be used in the present invention are selected from silicone oils and mixtures thereof.

As examples of silicone oils, we may notably mention polydimethylsiloxanes (PDMS), phenylated polyorganosiloxanes such as phenyltrimethicones, phenyltrimethylsiloxy-diphenylsiloxanes, diphenylmethyldimethyltrisiloxanes, diphenyldimethicones, phenyldimethicones, polymethyl-phenylsiloxanes, optionally fluorinated; polysiloxanes modified with fatty acids, fatty alcohols or polyoxyalkylenes, fluorinated silicones, perfluorinated silicone oils, aminated silicone oils.

Among preferred silicone oils, we may mention polydimethylsiloxanes, polymethylphenylsiloxanes, and mixtures thereof.

These silicone oils can optionally comprise alkyl, hydroxyl or alkoxy groups at the end of the silicone chain or pendant, for example polydimethylsiloxanes with trimethylsilyl end groups and polydimethylsiloxanes with dimethylsilanol end groups.

As examples of polydimethylsiloxanes with trimethylsilyl end groups, we may notably mention those having a viscosity from $5 \cdot 10^{-6}$ to 2.5 m$^2$/s at 25° C. and preferably $1 \cdot 10^{-5}$ to 1 m$^2$/s. The viscosity of the silicones is for example measured at 25° C. according to standard ASTM 445 Appendix C.

Among these polyalkylsiloxanes, we may mention, non-exhaustively, the following commercial products:
- the SILBIONE oils of series 47 and 70 047 or the MIRASIL oils marketed by RHONE POULENC such as for example the oil 70 047 V 500 000;
- the oils of the MIRASIL series marketed by the company RHODIA;
- the oils of the 200 series from the company DOW CORNING such as more particularly DC200 of viscosity 60 000 cSt;
- the oils sold under the trade name Belsil DM 300000 and Belsil DM 60000 by the company Wacker Chemie AG;
- the VISCASIL oils from GENERAL ELECTRIC and certain oils of the SF series (SF 96, SF 18) from GENERAL ELECTRIC.

We may also mention the polydimethylsiloxanes with dimethylsilanol end groups (Dimethiconol according to the CTFA designation) such as the oils of the 48 series from the company RHODIA.

As silicone oil usable in the invention, we may also mention the linear or cyclic silicones, and in particular with from 2 to 7 silicon atoms. We may notably mention octamethylcyclotetrasiloxane, decamethylcyclopentasiloxane, hexadecamethylcyclohexasiloxane, heptamethylhexyltrisiloxane, heptamethyloctyltrisiloxane and mixtures thereof.

The oils that are particularly preferred within the scope of the present invention are polydimethylsiloxanes and mixtures thereof.

The oil or oils as defined above is/are preferably present in an amount between 0.1 and 50 wt. %, more preferably in an amount between 1 and 30 wt. % relative to the weight of the composition.

The composition according to the invention can further comprise one or more vegetable oils.

In particular, "vegetable oil" means an oil as defined above, extracted from a species belonging to the vegetable kingdom.

The vegetable oil or vegetable oils used according to the invention are different from the volatile linear alkanes as defined previously and are selected from the vegetable oils usually employed in the field of cosmetics.

As examples of vegetable oil usable in compositions of the invention, we may mention camelina oil, sweet almond oil, argan oil, avocado oil, peanut oil, camellia oil, safflower oil, calophyllum oil, colza oil, copra oil, coriander oil, cucurbit oil, wheatgerm oil, jojoba oil or liquid jojoba wax, linseed oil, macadamia oil, maize germ oil, hazelnut oil, walnut oil, vernonia oil, apricot kernel oil, olive oil, evening primrose oil, palm oil, passionflower oil, grapeseed oil, rose oil, castor oil, rye oil, sesame oil, rice bran oil, soya oil, sunflower oil, and mixtures thereof.

Among the aforementioned vegetable oils, the following are preferably used: camelina oil, sweet almond oil, olive oil, argan oil, avocado oil, colza oil, jojoba oil or liquid jojoba wax, soya oil, sunflower oil, and more preferably camelina oil, sweet almond oil, avocado oil, jojoba oil or liquid jojoba wax, and mixtures thereof, and more preferably camelina oil and sweet almond oil.

The composition according to the invention can further comprise one or more conventional additives well known by a person skilled in the art, such as associative or non-associative, ionic, namely cationic or anionic, non-ionic, or amphoteric polymers, $C_{10-30}$ fatty alcohols, polyols, proteins, vitamins, reducing agents, plasticizers, emollients, anti-foaming agents, hydrating agents, pigments, clays, mineral fillers, UV filters, mineral colloids, peptizing agents, solubilizers, perfumes, preservatives, anionic, cationic, non-ionic or amphoteric surfactants, pearlescent agents, propellants, and mineral or organic thickeners.

A person skilled in the art will take care to select any additives and their amount so that they do not adversely affect the properties of the compositions of the present invention.

These additives are generally present in the composition according to the invention in an amount in the range from 0 to 20 wt. % relative to the total weight of the composition.

The compositions according to the invention can be in the form of a lotion of varying thickness, or a gel.

The invention also relates to a method of cosmetic treatment of keratinous materials, preferably of keratin fibres such as the hair, which consists of applying an effective amount of a cosmetic composition as described above on said materials, and optionally rinsing after an optional pause.

When the composition according to the invention is applied, it is optionally left on the hair for about ½ min to 5 minutes, optionally followed by rinsing with water.

The following examples are given for the purpose of illustration of the present invention.

In the following examples, all quantities are given as percentage by weight of substance as it is, relative to the total weight of the composition, unless stated otherwise.

EXAMPLES

Example 1

The following non-rinse care composition was prepared from the ingredients shown in the following table.

| | |
|---|---|
| Isopropyl myristate | 77.8% |
| Polydimethylsiloxane sold under the trade name Belsil DM 300000 by the company Wacker Chemie AG | 20% |
| Mixture predominantly consisting of n-undecane and n-tridecane according to example 2 of application WO 2008/155059. | 2% |
| Perfume | 0.2% |

This composition was applied on the hair. Excellent performance in smoothness and shine was observed.

Example 2

The following non-rinse care composition was prepared from the ingredients shown in the following table.

| | |
|---|---|
| Isopropyl myristate | 75% |
| Polydimethylsiloxane sold under the trade name Belsil DM 300000 by the company Wacker Chemie AG | 5% |
| Polydimethylsiloxane sold under the trade name Wacker Belsil DM 60000 by the company Wacker Chemie AG | 1% |
| Mixture predominantly consisting of n-undecane and n-tridecane according to example 2 of application WO 2008/155059 | 18.8% |
| Perfume | 0.2% |

This composition was applied on the hair. Easier shaping was observed.

Example 3

The following non-rinse care composition was prepared from the ingredients shown in the following table.

| | |
|---|---|
| Isopropyl myristate | 50% |
| Polydimethylsiloxane sold under the trade name Belsil DM 300000 by the company Wacker Chemie AG | 4% |
| Polydimethylsiloxane sold under the trade name Wacker Belsil DM 60000 by the company Wacker Chemie AG | 3% |
| Mixture of n-undecane and n-tridecane according to example 2 of application WO 2008/155059 | 42.8% |
| Perfume | 0.2% |

This composition was applied on the hair. Easier shaping was observed, as well as excellent performance in visual smoothness and feel.

Example 4

The following non-rinse care composition was prepared from the ingredients shown in the following table.

| | |
|---|---|
| Isopropyl myristate | 15% |
| Sweet almond oil | 7% |
| Triglycerides of caprylic/capric acids (60/40) (MYRITOL 318 from COGNIS) | 15% |
| Refined camelina oil | 7% |
| Mixture predominantly consisting of n-undecane and n-tridecane according to example 2 of aspplication WO 2008/155059 | 55% |
| Perfume | 1% |

This composition was applied on the hair. An excellent feel of wet hair and of dry hair was observed, which was notably reflected in less transfer of the composition onto the hands, after passing the hands through the hair.

Example 5

The following non-rinse care composition was prepared from the ingredients shown in the following table.

| | |
|---|---|
| Isopropyl myristate | 14% |
| Polydimethylsiloxane sold under the trade name Belsil DM 300000 by the company Wacker Chemie AG | 15.4% |
| Mixture predominantly consisting of n-undecane and n-tridecane according to example 2 of application WO 2008/155059 | 64.9% |
| 2-Ethylhydexyl 4-methoxycinnamate (PARSOL MCX from DSM NUTRITIONAL PRODUCT) | 0.5% |
| Ethanol | 5% |
| Perfume | 0.2 |

This composition was applied on the hair. Excellent properties of smoothness, feel and lightness were observed.

Example 6

The following non-rinse care composition was prepared from the ingredients shown in the following table.

| | |
|---|---|
| Isopropyl myristate | 50% |
| Polydimethylsiloxane sold under the trade name Belsil DM 300000 by the company Wacker Chemie AG | 4% |
| Polydimethylsiloxane sold under the trade name Wacker Belsil DM 60000 by the company Wacker Chemie AG | 3% |
| Mixture of n-dodecane and n-tetradecane sold under the trade name Vegelight 1214 by the company Biosynthis | 42.8% |
| Perfume | 0.2% |

This composition was applied on the hair. Easier shaping was observed, as well as excellent performance in visual smoothness and feel.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials. Terms such as "contain(s)" and the like as used herein are open terms meaning 'including at least' unless otherwise specifically noted. The term "mentioned" notes exemplary embodiments, and is not limiting to certain species. As used herein the words "a" and "an" and the like carry the meaning of "one or more." Where a modifying term is contained in parentheses, such as "(un-crosslinked) amphiphilic polymer," two things are described, one with the modifying term and one without the modifying term.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A method for the treatment of keratin fibres, comprising applying to said keratin fibers:
    one or more volatile linear alkanes,
    one or more liquid fatty esters of $C_{12-30}$ mono- or dicarboxylic acid and of C1-30 monohydric alcohol, and
    from 1 to 30% of one or more silicone oils,
    in a medium having a water content below 5 weight %, in a weight ratio of volatile linear alkane(s) to liquid fatty ester(s) of less than 5.

2. The method according to claim 1, wherein the volatile linear alkane is a linear alkane having from 7 to 15 carbon atoms.

3. The method according to claim 1, wherein the volatile linear alkane is selected from the group consisting of n-heptane, n-octane, n-nonane, n-decane, n-undecane, n-dodecane, n-tridecane, n-tetradecane, n-pentadecane and mixtures thereof.

4. The method according to claim 3, wherein the volatile linear alkane is selected from the group consisting of n-nonane, n-undecane, n-dodecane, n-tridecane, n-tetradecane, and mixtures thereof.

5. The method according to claim 1, wherein the volatile linear alkane is of vegetable origin.

6. The method according to claim 1, wherein the liquid fatty ester of $C_{12-30}$ mono- or dicarboxylic acid and of $C_{1-30}$ monohydric alcohol is selected from the group consisting of ethyl laurate, butyl laurate, hexyl laurate, isohexyl laurate, isopropyl laurate, methyl myristate, ethyl myristate, butyl myristate, isobutyl myristate, isopropyl myristate, 2-octyldodecyl myristate, 2-ethylhexyl monococoate, ethyl palmitate, isopropyl palmitate, isobutyl palmitate, 2-ethylhexyl palmitate, butyl stearate, isopropyl stearate, isobutyl stearate, isocetyl stearate, isostearyl isostearate, isopropyl isostearate, 2-ethylhexyl stearate, 2-ethylhexyl hydroxystearate, decyl oleate, diisopropyl sebacate, isononyl isononanoate, tridecyl neopentanoate, isocetyl neopentanoate, isostearyl neopentanoate, octyldodecyl neopentanoate, isoarachidyl neopentanoate, and mixtures thereof.

7. The method according to claim 1, wherein the weight ratio of volatile linear alkane(s) to liquid fatty ester(s) is in the range from 0.1 to 4.9.

8. A composition comprising, in a medium having a water content below 5 weight %:
    one or more volatile linear alkanes,
    one or more liquid fatty esters of a $C_{12-30}$ mono- or dicarboxylic acid and of a $C_{1-30}$ monohydric alcohol in a weight ratio of volatile linear alkane(s) to liquid fatty ester(s) of greater than or equal to 0.1 and less than 5, and
    from 1 to 30% of one or more silicone oils.

9. The composition according to claim 8, wherein the volatile linear alkane(s) are present in a content in the range from 0.5 to 90 wt. % relative to the total weight of the composition.

10. The composition according to claim 8, wherein the liquid fatty ester(s) are selected from the group consisting of ethyl laurate, butyl laurate, hexyl laurate, isohexyl laurate, isopropyl laurate, methyl myristate, ethyl myristate, butyl myristate, isobutyl myristate, isopropyl myristate, 2-octyldodecyl myristate, 2-ethylhexyl monococoate, ethyl palmitate, isopropyl palmitate, isobutyl palmitate, 2-ethylhexyl palmitate, butyl stearate, isopropyl stearate, isobutyl stearate, isocetyl stearate, isostearyl isostearate, isopropyl isostearate, 2-ethylhexyl stearate, 2-ethylhexyl hydroxystearate, decyl oleate, diisopropyl sebacate, isononyl isononanoate, tridecyl neopentanoate, isocetyl neopentanoate, isostearyl neopentanoate, octyldodecyl neopentanoate, isoarachidyl neopentanoate, and mixtures thereof.

11. The composition according to claim 8, wherein the silicone oils are selected from the group consisting of polydimethylsiloxanes, polymethylphenylsiloxanes, and mixtures thereof.

12. The composition according to claim 8, further comprising at least one additive selected from the group consisting of associative polymers, non-associative polymers, ionic polymers, non-ionic polymers, amphoteric polymers, polyols, proteins, vitamins, reducing agents, plasticizers, emollients, anti-foaming agents, hydrating agents, pigments, clays, mineral fillers, UV filters, mineral colloids, peptizing agents, solubilizers, perfumes, preservatives, surfactants, pearlescent agents, propellants, mineral thickeners, organic thickeners, and mixtures thereof.

13. A method of treatment of a keratinous material, comprising application of the composition according to claim 8 to said keratinous material.

14. The method of claim 13, wherein said keratinous material is hair.

15. The method of claim 1, wherein said keratin fibers are hair.

* * * * *